United States Patent [19]
Grasshoff et al.

[11] Patent Number: 5,616,451
[45] Date of Patent: Apr. 1, 1997

[54] METHOD OF IMAGING USING A POLYMERIC PHOTORESIST HAVING PENDANT VINYLBENZYL THYMINE GROUPS

[75] Inventors: J. Michael Grasshoff, Hudson; Lloyd D. Taylor, Lexington; John C. Warner, Norwood, all of Mass.

[73] Assignee: Polaroid Corporation, Cambridge, Mass.

[21] Appl. No.: 449,017

[22] Filed: May 24, 1995

Related U.S. Application Data

[62] Division of Ser. No. 242,253, May 13, 1994, Pat. No. 5,455,349.

[51] Int. Cl.$^6$ ............................................. G03F 7/30
[52] U.S. Cl. ........................................... 430/325; 430/270.1
[58] Field of Search .................................... 430/536, 363, 430/325, 270.1; 526/262

[56] References Cited

U.S. PATENT DOCUMENTS

| | | | |
|---|---|---|---|
| 4,128,706 | 12/1978 | Seita et al. | 526/46 |
| 4,563,411 | 1/1986 | Bronstein-Bonte | 430/213 |
| 5,039,813 | 8/1991 | Fazio et al. | 548/228 |
| 5,395,731 | 3/1995 | Grasshoff et al. | 430/213 |

OTHER PUBLICATIONS

Functional Monomers and Polymers CLXVIII. Syntheses and Photoreactions of Poly(methacrylate)s Containing Thymine Bases, M.J. Moghaddam, et al., Polymer Journal, vol. 21, No. 3, pp. 203–213 (1989).

Thymine Polymers as High Resolution Photoresists and Reversible Photo–recording Materials, Y. Inaki, Polymer News, 1992, vol. 17, pp. 367–371.

Photodimerization of Thymine–Containing Polymers: Applicability To Reversible Photoresists, K. Takemoto, et al., J. Macromol. Sci–Chem., A25(5–7), pp. 757–765 (1988).

Graft Copolymers Containing Nucleic Acid Bases and L–α–Amino Acids, C.G. Overberger, et al., Journal of Polymer Science, Polymer Chemistry Edition vol. 17, pp. 1739–1758 (1979).

Photolysis of Polyamides Containing Thymine Photodimmer Units in the Main Chain and Application to Deep–UV Positive Type Photoresists, M.J. Moghaddam, et al., Polymer Journal, vol. 22, No. 6, pp. 468–476 (1990).

Synthesis and Optical Properties of Polyethylenimine Containing L–Proline and Optically Active Thymine Derivatives, C.G. Overberger, et al., Journal of Polymer Science, Polymer Chemistry Edition, vol. 18, pp. 1433–1446.

Hoebel, in Annelen der Chemie, 353, 251–255 (1907).

*Primary Examiner*—Joseph L. Schofer
*Assistant Examiner*—Wu C. Cheng
*Attorney, Agent, or Firm*—Louis G. Xiarhos

[57] ABSTRACT

Multi-functional vinylbenzyl and vinylphenyl pendant thymine (and uracil) groups are disclosed. The monomers can be used for the production of polymers useful in photoresist and other compositions as a function of the crosslinking reactivity of the pendant groups. Images in polymer are provided by exposure to actinic radiation (e.g., UV), containing such polymer and by solvent removal of non-exposed regions.

9 Claims, No Drawings

METHOD OF IMAGING USING A POLYMERIC PHOTORESIST HAVING PENDANT VINYLBENZYL THYMINE GROUPS

This application is a division of application Ser. No. 08/242,253 filed May 13, 1994, now U.S. Pat. No. 5,455,349, issued Oct. 3, 1995.

REFERENCE TO RELATED APPLICATION

The present application is related to the copending patent application of J. Michael Grasshoff, et al. for COPOLYMERIC MORDANTS AND PHOTOGRAPHIC PRODUCTS AND PROCESSES CONTAINING SAME, U.S. Ser. No. 08/242,298, filed May 13, 1994, now U.S. Pat. No. 5,395,731, issued Mar. 7, 1995, discloses and claims certain vinylbenzyl (and vinylphenyl) thymine (and uracil) polymeric mordants useful in the production of images by photographic diffusion transfer processing.

BACKGROUND OF THE INVENTION

This invention relates to certain vinylbenzyl thymine (VBT) monomers and polymers. More particularly, it relates to a class of polymerizable vinylbenzyl (and vinylphenyl) monomers having pendant functional thymine (and uracil) groups useful in the production of polymeric coatings and articles, including photoresists, which can be imaged by a photolyric (crosslinking) reaction.

As used herein, and except as otherwise indicated, the recitations "VBT" and "VBT monomer(s)" are sometimes used to refer to a class of polymerizable vinylbenzyl (and vinylphenyl) monomers having pendant thymine (or uracil) group. The recitation "VBT" refers also to the specific compound 1-vinylbenzyl -thymine. The nature of compounds within the aforementioned class will be apparent from the description which follows, including the formulae and the examples.

Thymine itself and polymers containing thymine units are well known and have been described in numerous patents and other publications. Examples of polymers containing pendant thymine groups include DNA or synthethic polymers such as polyethyleneimine, acrylic esters, acrylamides or poly-lysine and have been described, for example, by M. J. Moghaddam, et al., in Polym. J., 22, 468–476 (1990); by K. Takemoro, et al., in J. Macromol. Sci-Chem., A25 (5–7), 757–765 (1988); by C. G. Overberger, et al., in J. Polym. Sci., Polym. Chem. Ed., 17, 1739–1769 (1979); and by C. G. Overberger, et al., in J. Polym. Sci., Polym. Chem. Ed. , 18, 1433–1446 (1980).

Prior to the instant invention, monomers and polymers wherein thymine units are attached to vinylphenyl or vinylbenzyl groups were unknown. It will be appreciated that there will be considerable interest in the (vinylbenzyl) thymine monomer which can be used for the production of a variety of useful polymeric materials. A principal use of the VBT monomer is in the area of photoresist coatings than can be imaged by exposure to UV radiation. Another use of the VBT monomer is as a comonomer in the production of mordant copolymers based upon quaternary compounds, as is described, for example, in the aforementioned U.S. Patent Application of J. Michael Grasshoff, et al. (Attorney Docket No. 7919).

The use of photopolymerization reactions in the printing and graphic arts fields for the production of relief and lithographic printing plates has been well known. Suitable methods of the production of plates for the printing and graphic industries are described, for example, in *Neblette's Handbook of Photography And Repography, Seventh Edition*, pp. 439–40 (1977). Typically, a monomeric compound on a suitable plate support material will be selectively exposed to a source of light so as to effect a photopolymerization (insolubilization) in exposed areas. The difference in solubility, between unexposed and exposed (polymerized) areas, permits easy development.

The principles of photopolymerization are also utilized in photoengraving and lithographic plate-making by the use of polymers whose molecules are able to crosslink under the action of light to form a three-dimensional molecular network. Typically, the photo-crosslinked polymer will be insoluble, and will be soluble only in powerful solvent mixtures of the type used in paint stripping. Stencils produced by the photo-crosslinking reaction are images which are highly resistant to commonly used solutions; solvent development is used to remove the original polymer from unexposed areas.

In U.S. Pat. No. 3,081,168 (issued Mar. 12, 1963 to R. M. Leekly et al.) the production of relief plates using polyamides as a preformed polymer is described. Photosensitivity is imparted to the polyamide, which is carried on a support, by including with the polyamide, a photopolymerizable unsaturated compound. Following a selective exposure to light, which induces a decrease in solubility in exposed areas, unexposed areas are removed with a developer. After development, the base material e.g., metal) can be etched by chemical etching or abrasive blast to form a relief image in the base material. If desired, an offset plate can be prepared by coating the photosensitive polyamide composition onto a hydrophilic support. The image obtained upon photoexposure and development will carry an ink and the wet support will resist ink.

In the production of plates by resort to photoreaction chemistry, a reactive and photopolymerizable monomeric compound will oftentimes be employed. The compounds are frequently liquid or in a gaseous form which may hamper efficient handling and the production of coatings suited to photopolymerization. Preformed polymers which are photo-crosslinkable may exhibit limited photo-reactivity or sensitivity. Accordingly, it will be appreciated that there will be application in photosensitive imaging schemes for a polymeric compound which can be conveniently coated from an aqueous medium onto a suitable substrate or carrier material and which can be readily converted, by a chemical modification induced by exposure to irradiation, to an insoluble or hydrophobic material.

SUMMARY OF THE INVENTION

It has been found according to the present invention that a multi-functional monomer, 1-(vinylbenzyl) thymine (VBT), is made in one step by allowing thymine to react with vinylbenzy chloride directly, without requiring blocking and deblocking of the 3-position. This invention also concerns the preparation of other related monomers such as 1-(vinylbenzyl) uracil (VBU), 1-(vinylbenzyl) -3-methylthymine (VBMT), and 1- (vinylphenyl) thymine (VPT). In a product aspect, the present invention includes a polymerizable monomer according to the formula:

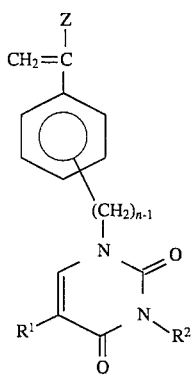

Formula I wherein each of $R^1$ and $R^2$ is hydrogen or alkyl (e.g., methyl); Z is hydrogen or methyl; and n is an integer 1 or 2.

Monomers according to Formula (I) are especially useful in preparing copolymers from aqueous systems, both water soluble and emulsion types, enabling the production of polymers and composites having superior properties, without required use of hazardous solvents.

According to another product aspect of the present invention, there is provided a copolymer having copolymerized repeating units derived from a Formula-I ethylenically unsaturated polymerizable monomer; and copolymerized repeating units from a different copolymerizable ethylenically unsaturated monomer. A preferred copolymer of this type is a copolymer including repeating units from a vinylbenzyl quaternary ammonium compound, the polymer having the formula:

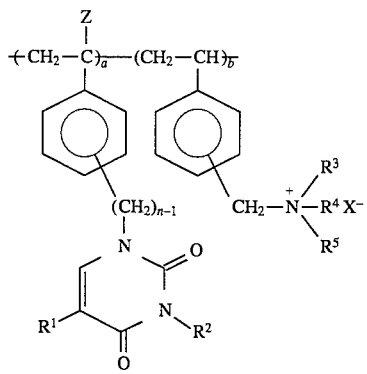

Formula II wherein each of $R^1$, $R^2$ and n has the meaning previously defined; each of a and b represent a molar proportion of each of the respective repeating units; each of $R^3$, $R^4$, and $R^5$ is independently alkyl (e.g., methyl, ethyl, propyl, butyl); substituted-alkyl (e.g., hydroxyethyl, hydroxypropyl); cycloalkyl (e.g., cyclohexyl); aryl (e.g., phenyl, naphthyl); aralkyl (e.g., benzyl); alkaryl (e.g., tolyl); or at least two of $R^3$, $R^4$, and $R^5$ together with the quaternary nitrogen atom to which they are bonded complete a saturated or unsaturated, substituted or unsubstituted nitrogen-containing heterocyclic ring (e.g., morpholino, piperidino, or 1-pyridyl); and X is a counteranion (e.g., halide). These copolymers have the desired functionality and versatility of the pendant thymine groups and, as a function of control of the nature of the $R^3$, $R^4$, and $R^5$ groups, exhibit wettability by water and coatability from aqueous media.

According to one of its product aspects, the present invention provides a photosensitive article comprising a suitable substrate material carrying a layer of photosensitive VBT polymer, the polymer being adapted, upon exposure to actinic radiation, to conversion to a water-insoluble polymeric material.

According to one of its method aspects, there is provided a method whereby an article carrying a layer of photosensitive VBT polymer is irradiated sufficiently to induce a photochemical modification of the polymer and resulting insolubilization. Unreacted regions are removed by solvent (development) treatment. A preferred method comprises selectively irradiating an article carrying a water-based layer of photosensitive VBT polymer, to convert exposed areas to a water-insoluble material; and washing from the article, in areas of non-exposure, the unreacted VBT polymer; thereby to provide an image in water-insoluble polymeric material. Certain novel monomers, polymers, compositions containing photosensitive VBT polymers, and methods for the use thereof are provided by the present invention. Objects of the present invention, details, constructions, operations, uses, advantages and modifications thereof will be apparent from the following description.

DETAILED DESCRIPTION OF THE INVENTION

As indicated previously, the present invention is directed toward certain vinylbenzyl thymine monomers and polymers represented, for example, by Formulas (I) and (II), respectively. In general, the present invention includes a class of novel polymerizable monomers according to the formula

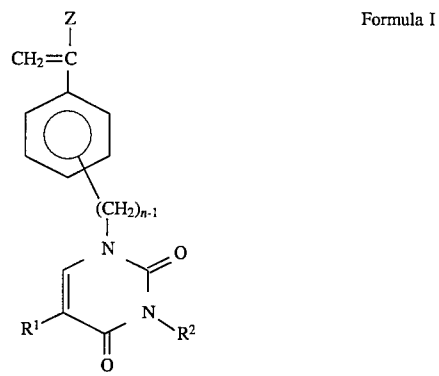

Formula I wherein $R^1$, $R^2$, Z and n are as previously defined.

A preferred copolymerizable monomer of Formula (I) is 1-(vinylbenzyl) thymine (VBT) and is shown by formula (III)

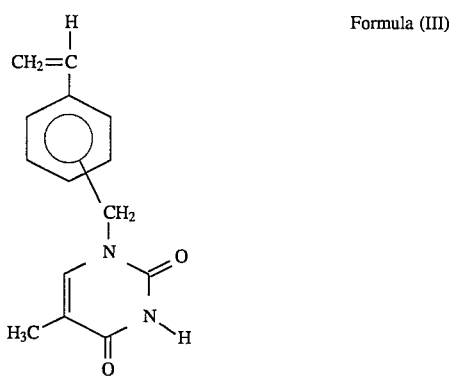

Formula (III)

1-VBT is made in one step by allowing thymine to react with vinylbenzyl chloride directly, without requiring blocking and deblocking of the 3-position.

The VBT monomer has interesting properties and can thus impart to polymers correspondingly valuable properties. Polymers which have VBT units incorporated therein will possess: (a) A chemically stable linkage between the styrene and thymine (e.g., no hydrolysis as with esters); (b) A benzene ring as a spacer between the thymine and the backbone which may give rise to π—stacking interactions; (c) Thymine units which can form strong hydrogen bonds, including three linear coherent ones with a proper partner such as a 2,6-diamidopyridine derivative; (d) An imide nitrogen having a pKa of about 9. When iononized above pH 9, the polymers swell and may form poly-electrolyte complexes with polycations; and (e) An imide nitrogen that can be alkylated or reversibly blocked to form polymers that are more soluble. This also affords an opportunity to covalently bond a functional group which will then be incorporated in the polymer or membrane.

The polymers or copolymers are photo-sensitive and are readily cross-linked with UV light giving still another way of improving bulk properties of a material or film. Emulsion or latex polymers can be made which have VBT units incorporated. Films made from these emulsions also show the photo-cross-linking reaction.

The unusual polyfunctionality of the VBT monomer is shown in Formual IV as follows:

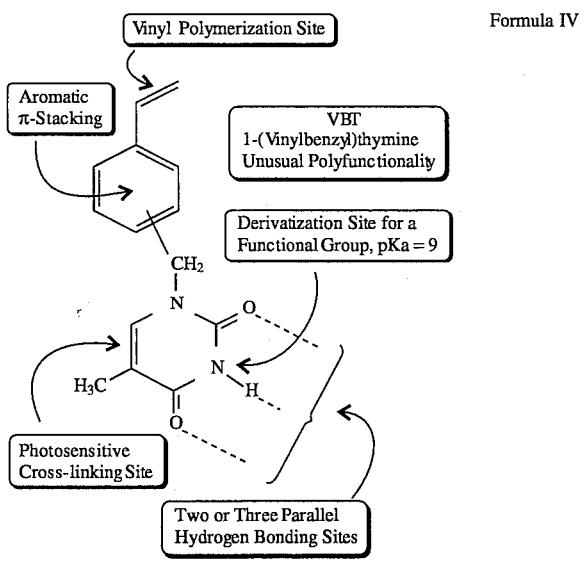

Formula IV

Built into the structure of VBT are several exploitable functionalities. The vinyl group provides the ability to copolymerize the material with a wide variety of monomers, including acrylates and styrenes. This versatility allows for the preparation of polymeric thymines whose solubilities range from water to organic soluble. The triple hydrogen bonding pattern presented by the cyclic imide group allows for the non-covalent complexation of these materials as self associated aggregates or with suitable functionalized complexation conjugates. The imide nitrogen at N-3 is capable of derivatization via alkylation. Substitution at this position prevents the triple hydrogen bonding complexation and has dramatic consequence to the bulk properties of these materials. Most importantly, the unsaturated bond at postions 5 and 6 is where the photoreactivity is centered, allowing for 2π+2π cyclization.

In the production of products of the invention, a layer or coating of a VBT polymer is converted by actinic radiation to a polymeric material exhibiting organic solvent or water insolubility. The nature of such insolubility will depend principally upon the nature of the ethylenically unsaturated monomer copolymerized with the Formula-I VBT monomer. Examples of suitable copolymerizable monomers are described hereinafter. In general, the utilization of copolymerizable monomers which do not promote water solubility (e.g., the acrylates, such as is shown in EXAMPLE 7) will dictate coating of the copolymer from an organic solvent. In the case of the production of images in such copolymer, organic solvent development will be employed for removal of non-exposed (unreacted) areas of the polymer. Exposed regions, rendered insoluble or less soluble in the organic solvent will remain as a polymeric image on the coated substrate. The employment of a copolymerizable monomer which promotes water solubility will be preferred, so that a water-based photoresist can be coated. Non-exposed regions can be washed away with water, leaving exposed insolubilized regions of copolymer.

When a VBT polymer is subjected to photolysis, the resulting chemical modification (photo-cross-linking with 2+2 dimerization) is accompanied by a substantial change in polymer properties. This substatial change in polymer properties makes possible the application of VBT polymers to the production of various articles, including photoresists, stencil coatings, duplicating pads, lithographic and relief plates, printed circuit boards and chemically etched electrode patterns on glass or other supports. Variations in the nature of the polymer can be used to accomodate particular applications.

The chemical conversion (photo-cross-linking and 2+2 dimerization) can be illustrated by resort to the following scheme showing the conversion of a polymer having VBT units to the corresponding photo-crosslinked polymer:

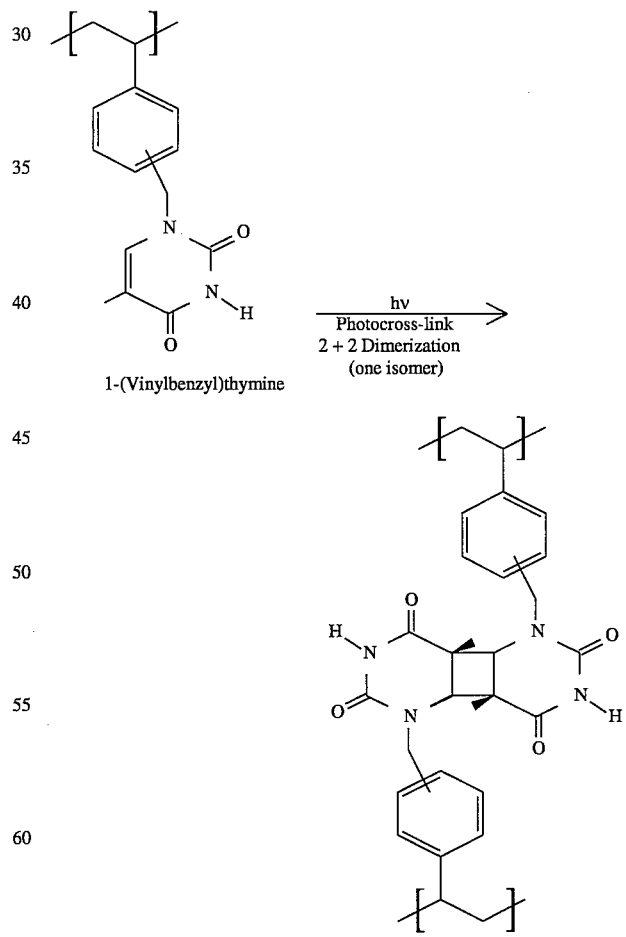

The VBT polymers of this invention can be homopolymers or copolymers, including graft or block copolymers. The copolymers can contain units provided by copolymerization with various ethylenically unsaturated monomers such as alkyl acrylates, alkyl methacrylates, acrylamides, methacrylamides and styrenes. In general, these comonomeric units are utilized to provide particular predetermined properties to the polymer, such as coatability and viscosity and, in particular, polymerizability.

In general, the polymers employed herein will contain the photo-reactive VBT repeating units in an amount sufficient to allow for appreciable conversion from a relatively soluble condition to a condition of relative insolubility. In the copolymers, the proportion of photo-reactive VBT units to total units will vary depending on the nature of the particular photo-reactive units employed, the nature of the comonomeric or any polymeric material that may be utilized therewith, and upon the particular application and product requirements or characteristics desired.

A preferred comonomeric unit that can be included in a VBT polymer of the present invention is the quaternary-containing (water-solubility promoting) unit obtained from the polymerizable quaternary-containing monomer of the formula

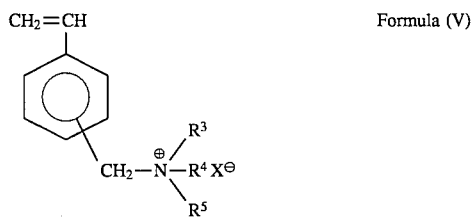

Formula (V)

wherein each of $R^3$, $R^4$, $R^5$, and X has the meaning previously defined.

This monomer is readily polymerizable with the VBT units hereof. A preferred copolymer is a copolymer of VBT and vinylbenzyl trimethylammonium units. The quaternary-containing units, also being cationic, are dye mordant compounds and are receptive to anionic dyes. Good photoimaging results are provided upon irradiation of this preferred copolymer. Other ethylenically unsaturated comonomers can, however, be used and examples of such include styrenes (e.g., styrene, 4-acetoxy-styrene, 4-t-butyl-styrene); acrylic acid; methacrylic acid; acrylamides (e.g., diacetone acrylamide; 2-acrylamido-2-methylpropane sulfonic acid; N-methyl acrylamide; methacrylamide); and acrylates (e.g., ethyl acrylate; butyl acrylate; methyl methacrylate).

The ethylenically unsaturated polymerizable monomers can be polymerized using known polymerization techniques such as solution polymerization using free radical or redox initiation and known emulsion polymerization methods. Relative proportions of the Formula-I and other polymerizable monomer(s) can vary widely, depending upon a particular product or system. In the case of a copolymer suited as a mordant in a photographic diffusion transfer product and method, such as a copolymer of Formula II, the ratio of a:b can vary in the molar range of from 1:10 to 10:1. A preferred ratio is from 1:2.5 to 1:9 (e.g., 1:4).

The VBT-containing monomers can be converted to their corresponding photo-crosslinked form by using a source of actinic irradiation of sufficient intensity. In general, ultraviolet radiation provides good results; other sources of actinic irradiation can, however, be employed. It will be appreciated that the amount of irradiation required to effect the desired conversion will vary with the wavelength and the intensity of the radiation source and will vary with the absorption properties of the VBT units of the polymer employed. Appropriate exposure times and conditions can be employed depending upon these considerations. In general, a source of ultraviolet irradiation can be used in conjunction with exposure times in the range from less than one to about 30 minutes or more.

A layer of the polymer can be applied from solution to a suitable substrate which is then subjected to exposure to a source or irradiation sufficient to effect the desired conversion of the VBT unit to the corresponding photo-crosslinked polymer. Water can be employed and will be a preferred solvent material for the preparation of a coating composition which can be conveniently applied to the substrate by spraying, dipping, roll coating or the like. Other solvents, such as methylene chloride can, however, be used. A coating composition suited to application to various substrate materials will typically contain the desired VBT polymer in a concentration of about 2 to 6% by weight, although other concentrations can be used depending upon the particular polymer employed, the nature of the solvent utilized, the method of application and the nature of the particular substrate. Various additives such as surfactants, coating aids, viscosity-controlling agents, UV stabilizers, photoinitiators, sensitizers or the like can be included, provided that such agents do not interfere with the desired conversion of the VBT unit compound to the corresponding photo-crosslinked polymer.

The polymers can be used for the treatment of substrates such as glass, metal, plastic, such as polyethylene terephthalate or cellulose acetate, or fabrics. Sheets, swatches, scrims, ropes or other fibers can be sprayed, dipped or otherwise coated with the VBT compound and can be, then, subjected to actinic irradiation to provide a polymeric surface exhibiting insolubility, hydrophobicity or water repellency.

The resistance of the irradiated polymeric materials to water and other solvent materials, including solvent etching materials, allows for the use of the VBT polymers hereof in the production of articles wherein the irradiated polymer comprises an image pattern. Thus, a layer of a VBT polymer on a suitable substrate material can be exposed to actinic irradiation in an imagewise manner to provide a recordation or image in polymerized material. Exposure of the layer of VBT polymer can be accomplished through a negative, a photomask or the like. Unexposed areas can be removed by dissolution in water (or organic solvent, depending upon the solubility of the layer) to provide the desired image in the polymerized photoresist material.

There are a number of ways to produce images from the VBT-containing polymers. Typically, a thin film of photopolymer is cast from an appropriate solvent to a uniform coverage, e.g., λ20–100 mg/ft$^2$ (215–1075 mg/m$^2$). The film is then irradiated with a short wavelength UV light source (75–150 mJ/cm$^2$; 250–400 nm) through a stencil or target. Unreacted photopolymer is washed with an appropriate solvent. The dried films are stable, maintain color when any mordanting sites are present and are dyed, and resist physical removal by scratching of the image. The sensitivity of this type of system has been evaluated to be about 450 mJ/cm$^2$, i.e., the minimum exposure necessary to produce the tonable image.

There are several ways of making a pigment image. For example, a first sheet can be coated with a layer of pigment, e.g., carbon black, removable from the sheet. The pigment layer can then be coated with a photoresist layer of the invention, preferably, one having water-solubilizing groups conducive to preferred water development. VBT polymers having vinylbenzyl trimethylammonium units are especially useful. When the resulting element is exposed imagewise to actinic radiation, the photoresist is photohardened and non-exposed regions can be removed by water development, baring the underlying pigment layer. Then, a receptor sheet carrying adhesive can be laminated with heat onto the developed element. On separation of the sheets, bared pigment (in unexposed regions) is removed from the first sheet to the receptor sheet. In photoexposed regions, the photohardened polymer overlying the pigment layer prevents removal of the pigment to the receptor sheet.

Other imaging schemes based upon the use of a photo-cross-linkable layer containing a VBT copolymer, dyes, pigments, toners, sensitizers and the like can, however, be employed.

The following examples are illustrative of the present invention and it will be understood that the invention is not limited thereto. All parts and percentages are by weight, except as otherwise indicated.

EXAMPLE 1

In a 2-L 3-neck round bottom flask, equipped with stirrer, reflux condenser and addition funnel, water and aqueous KOH are mixed, followed by addition of thymine, 60 g (0.476 mol) at ambient temperature to give a clear solution. The rate of agitation is increased and EtOH is added over a period of ten minutes resulting in a fine dispersion of thymine potassium salt. Upon addition of the inhibitor (2,6-di-t-butyl-4-methylphenol, 0.3 g) and 73 g(0.478 mol) vinylbenzyl chloride (Dow Chemical, a 60/40 m/p isomer mixture), the batch is heated at gentle reflux for 6 hours and subsequently allowed to cool to room temp. Vacuum filtration (to remove KCl) renders a clear, slightly yellow solution which is subjected to solvent evaporation under reduced pressure (<30° C.) to yield a semi-solid residue. The product is taken up in 500 ml of warm toluene, followed by filtration to remove undissolved solid (consisting mostly of unreacted thymine). A small amount of high $r_f$ material (presumably dissolved thymine) is then removed by passing the toluene solution through a 1-inch layer of silica (placed on a coarse sintered-glass funnel). The filtrate is concentrated to about half its volume. To the heated pre-purified toluene solution is gradually added with stirring about 200 ml of hexane and the slightly cloudy mixture is allowed to cool to room temp. Seed crystals from a previous run are preferably added before transferring the batch to a refrigerator. Complete crystallization is attained after refrigeration for 24 hours. The slightly yellow crystals are filtered and washed with toluene/hexane 5:1 (v/v) and finally hexane. After recrystallization form toluene/hexane, 2:1 (v/v), and subsequent vacuum drying at room temperature, about 50 g of the pure compound is obtained, 45–50%, mp 110° C. The product was a monomer having the formula

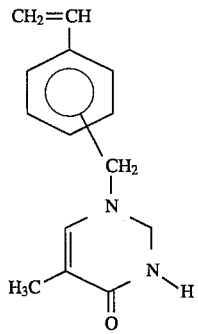

EXAMPLE 2

A mixture of 1-(vinylbenzyl) thymine [1.0 g, 6 mmol], iodomethane [0.94 g, 6.6 mmol] and potassium carbonate in 10 mL dimethylsulfoxide was stirred at room temperature for 48 hrs. The mixture was poured in 50 mL of water with stirring and allowed to stand overnight. The material was collected, washed with water followed by ether and dried to give 0.55 g [52%] of a white solid mp 87°–88 ° C. The product was a monomer having the formula

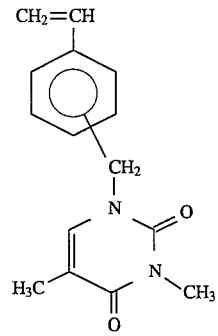

EXAMPLE 3

In a three necked round-bottomed flask, equipped with stirrer and drying tube, 35 g (0.23 mol) of AgOCN (dried in vacuo over $P_2O_5$) was covered with 95 ml of dry benzene. 20 g (0.15 mol) of β-methoxymethacryloyl chloride (Organic Consultants of Oregon) was added and the mixture was occasionally stirred until the exothermic reaction had subsided, followed by continuous stirring overnight. After addition of Celite and vacuum filtration, 18 g (0.15 mol) of p-vinyl aniline (Monomer-Polymer/Dejac Labs) was added to give 19 g of crude N-(β-methoxymethacryl)-N'-(p-vinylphenyl)urea, mp 153°–155° C. A 5 g sample of the urea was stirred in 20 ml of 2N NaOH at 50° C. overnight. Acidification and recrystallization from chloroform gave 2.5 g of pure 1-(p-vinylpheny)thymine as off white crystals, mp 185° C. (polymerizes). The product was a monomer having the formula

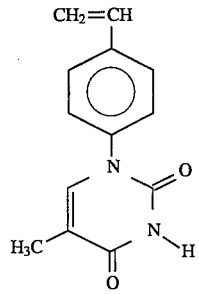

EXAMPLE 4

Uracil (20 g, 0.18 mol) was suspended in 750 ml DMF. Anhydrous potassium carbonate (49.2 g, 0.36 mol) was added and then stirred overnight. Vinylbenzyl chloride (63.6 g, 0.42 mol) was added and stirring was continued for the weekend. The gel-like mixture was filtered and the solid was washed with 50 ml of DMF. The DMF portions were combined and allowed to gently evaporate, making sure that the temperature never exceeded room temperature. A brownish residue which was very viscous and oily was obtained. Distilled water (250 ml) was added, followed by 150 ml chloroform. The mixture was transferred to a separatory funnel and the chloroform layer was removed and placed in an Erlenmeyer flask. The water layer was further extracted with two 150-ml portions of chloroform. All of the chloroform extracts were combined in the Erlenmeyer flask and dried over anhydrous sodium sulfate overnight. The chloroform was then removed under reduced pressure leaving a thick brown oily residue. The residue was placed in the refrigerator overnight. A white suspension was observed in the morning. The suspended mixture was then dissolved in warm ethanol and placed in the refrigerator for 4 h. A white precipitate was formed, which was then filtered and dried. The solid was recrystallized from ethanol and a total of 23.2 g (28.3% yield) was obtained. The product was a monomer having the formula

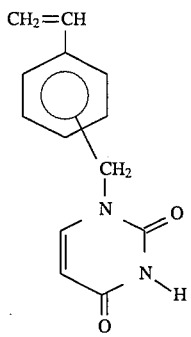

EXAMPLE 5

A solution of (vinylbenzyl)trimethylammonium chloride (TMQ) (3.5 g, 0.017 mol) and 1-VBT (1 g, 0.004 mol) was prepared in 2-propanol (40 ml). After adding 0.02 of AIBN, the solution was heated under nitrogen for 16 hrs. at 65° C., during which time the polymer precipitated. After washing with 2-propanol, the polymer was dissolved in water to make a 7.7% solution.

EXAMPLE 6

VBT latices were prepared by emulsion polymerization using recipes given in Table 1. A semicontinuous process of monomer addition was used to prepare copolymer latices. In this process, the seed formation was first completed; then the remaining monomer mixture was fed into the reactor at a constant feed-rate using a dropping funnel. The polymerization was carried out under a nitrogen atmosphere in a 500-ml four necked flask immersed in a constant-temperature bath at 85° C. and equipped with a reflux condenser, a stirrer, a dry nitrogen inlet, and an 150-ml graduated dropping funnel. Distilled, de-ionized water, Aerosol OT (di-2 ethylhexyl ester of sodium sulfosuccinic acid, American Cyanamid), and sodium bicarbonate were initially charged and maintained under constant agitation of 195 rpm for 30 minutes, followed by an addition of 5% of the monomer mixture and potassium persulfate initiator. After 20 minutes, the remaining monomer mixture was added continuously over a period of two hours. Three hours after the monomer addition was complete, the reaction was stopped, and a stable dispersion was obtained. Both scanning electron microscope and light scattering indicated the average particle size of these copolymer latices was in the range of 100 to 130 nm.

TABLE 1

| Latex Composition (wt %) | Sample | | | | | | |
|---|---|---|---|---|---|---|---|
| | 1 | 2 | 3 | 4 | 5 | 6 | 7 |
| 1-(vinylbenzyl)-thymine (VBT) | 10.0 | 10.0 | 10.0 | 20.0 | 10.0 | 20.0 | |
| 1-(vinylbenzyl-3-methylthymine (VBMT) | | | | | | | 10.0 |
| Styrene | 90.0 | | | | | | |
| n-Butyl methacrylate | | 32.9 | 27.8 | 38.7 | 35.8 | 37.4 | 32.9 |
| Methyl methacrylate | | 13.4 | 14.4 | 7.6 | 24.2 | 12.6 | 13.4 |
| Methacrylic acid | | 3.7 | 3.7 | 3.7 | | | 3.7 |
| Diacetone-acrylamide | | 30.0 | 30.0 | 30.0 | 30.0 | 30.0 | 30.0 |
| Carbomethoxy-methyl acrylate | | 10.0 | | | | | 10.0 |

EXAMPLE 7

A 5% solution of the 93.5/6.5 (mol %) methylmethacrylate/1-vinylbenzylthymine copolymer in methylene chloride was coated onto a clear polyethylene terephthalate sheet at a coverage of (about 30 mg/ft$^2$) and dried to a film. The resulting film was then photoexposed through a quartz resolution target for ten minutes, using a hand-held ultraviolet-radiation lamp source (Mineralight-, Model UVGL-25, VVP, Inc.) placed at a distance of two centimeters from the film and providing affluence of 150 mJ/cm$^2$ at wavelengths in the range of 250–400 nm. The film was then washed with methylene chloride to remove unreacted (non-exposed) regions of photopolymer, to provide a sheet carrying an image in photohardened polymer.

EXAMPLE 8

Onto a polyethylene terephthalate support substrate was coated uniformly to a coverage of about 20 mg/ft$^2$ (about 215 mg/m$^2$) a solution (2.8% in water) of the 80/20 copolymer of vinylbenzyl (benzyldimethyl) ammonium chloride and 1-vinylbenzlthymine. The coating was dried and then photoexposed through a quartz resolution target using the source and exposure conditions recited in EXAMPLE 7. After photoexposure, the film was washed with water to remove unreacted (non-exposed regions of) photopolymer. The film was then submerged in a suspension of dye (Acid Alizarin Violet N, Aldrich Chemical Company) for about five minutes and washed with water. A toned image was produced in areas of photoexposure.

EXAMPLE 9

Onto a polyethylene terephthalate support subsrate was coated uniformly to a coverage of about 20 mg/ft$^2$ (about 215 mg/m$^2$) a solution (2.8% in water) of the 80/20 copolymer of vinylbenzyl (benzyldimethyl) ammonium chloride and 1-vinylbenzylthymine). The coating was dried and then photoexposed through a quartz resolution target, using the source and exposure conditions recited in EXAMPLE 7. Onto the surface of the photoexposed layer was laminated a pigmented (carbon-bearing) donor sheet comprising a polyethylene terephthalate (PET) web carrying a layer of carbon black (CB) and polyvinylalcohol (PVA), at a ratio of CB/PVA of about 5/1. The lamination was conducted at 250° F., 60 ib/n$^2$ and three feet/minute 121° C.; 4.2 kg/cm$^2$; 0.91 m/min.), sufficient to laminate the donor sheet to the image.

Upon peeling of the PET donor web from the image, the carbon black/PVA layer was transferred therefrom and onto the image. The resulting photoexposed layer carrying the pigmented layer was then washed with water to remove from the support substrate non-exposed regions of photopolymer and overlying carbon. The result was an image in the remaining (exposed) regions, comprising photohardened polymer and corresponding overlying portions of the CB/PVA layer.

Although this invention has been described with reference to a series of preferred embodiments, it should be understood that changes in form and detail may be made without departing from the spirit and scope of the invention.

What is claimed is:

1. A method of forming an image in photo-cross-linked polymer comprising the steps of subjecting imagewise to actinic radiation, an article comprising a support carrying a layer of photosensitive polymer having repeating units of the formula

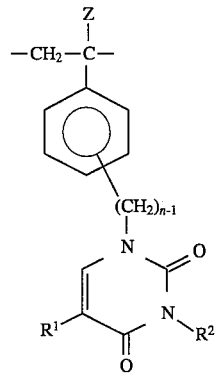

wherein each of $R^1$ and $R^2$ is hydrogen or alkyl; Z is hydrogen or methyl; and n is an integer 1 or 2; said layer being photo-cross-linkable in areas subjected to said actinic radiation;

and removing from said support areas of said layer not subjected to said radiation.

2. The method of claim 1 wherein said layer is a layer coated from an aqueous composition containing said polymer and said areas not subjected to said radiation are removed by aqueous washing.

3. The method of claim 1 wherein said polymer includes repeating units from an ethylenically unsaturated copolymerizable monomer having a pendant water-solubilizing group.

4. The method of claim 3 wherein said polymer has the formula

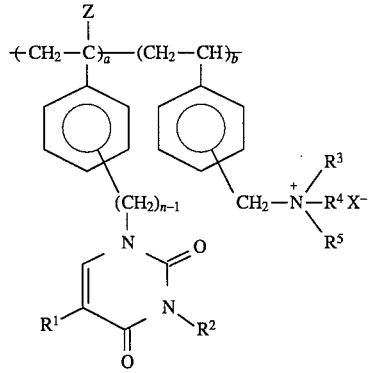

wherein each of $R^1$ and $R^2$ is hydrogen or alkyl; Z is hydrogen or methyl; n is an integer 1 or 2; each of a and b represents a molar proportion of each of the respective repeating units, in the range of from 1:10 to 10:1; each of $R^3$, $R^4$, and $R^5$ is independently alkyl; substituted-alkyl; cycloalkyl; aryl; aralkyl; alkaryl; or at least two of $R^3$, $R^4$, and $R^5$ together with the quaternary nitrogen atom to which they are bonded complete a saturated or unsaturated, substituted or unsubstituted nitrogen-containing heterocyclic ring; and X is a counteranion.

5. The method of claim 4 wherein $R^1$ is methyl; $R^2$ is hydrogen; Z is hydrogen; and n is the integer 2.

6. The method of claim 4 wherein the molar ratio of a:b is from 1:2.5 to 9:1.

7. The method of claim 6 wherein each of $R^3$, $R^4$ and $R^5$ is alkyl and $X^-$ is chloride.

8. The method of claim 7 wherein each of $R^3$, $R^4$ and $R^5$ is methyl.

9. The method of claim 1 wherein said layer is a layer coated from an organic composition containing said polymer and said areas not subjected to said radiation are removed by washing with an organic solvent therefor.

* * * * *